(12) United States Patent
Scheiner et al.

(10) Patent No.: US 7,532,414 B2
(45) Date of Patent: *May 12, 2009

(54) REFLECTIVE OPTICAL SYSTEM

(75) Inventors: David Scheiner, Ganei Yehuda (IL);
Michael Winik, Mezkeret Batya (IL);
Yakov Lyubchik, Kiryat Ekron (IL)

(73) Assignee: Nova Measuring Instruments, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/832,837

(22) Filed: Aug. 2, 2007

(65) Prior Publication Data

US 2007/0268591 A1    Nov. 22, 2007

Related U.S. Application Data

(63) Continuation of application No. 11/003,012, filed on Dec. 3, 2004, now Pat. No. 7,253,970.

(30) Foreign Application Priority Data

Jun. 17, 2004  (IL) .................................... 162617

(51) Int. Cl.
G02B 17/08 (2006.01)
G02B 27/14 (2006.01)

(52) U.S. Cl. .................... 359/727; 359/637; 359/730; 359/732

(58) Field of Classification Search ............. 359/637, 359/727, 730, 732
See application file for complete search history.

(56) References Cited

U.S. PATENT DOCUMENTS

| 2,628,533 | A | | 2/1953 | Oentjen |
| 4,170,401 | A | | 10/1979 | Yoder, Jr. et al. |
| 4,195,914 | A | * | 4/1980 | Hughes ................. 359/858 |
| 4,226,501 | A | | 10/1980 | Shafer |
| 4,395,095 | A | | 7/1983 | Horton |
| 4,747,678 | A | | 5/1988 | Shafer et al. |
| 5,071,240 | A | | 12/1991 | Ichihara et al. |
| 5,212,588 | A | | 5/1993 | Viswanathan et al. |
| 5,517,312 | A | | 5/1996 | Finarov |
| 5,604,344 | A | | 2/1997 | Finarov |
| 5,608,526 | A | | 3/1997 | Piwonka-Corle et al. |
| 5,764,365 | A | | 6/1998 | Finarov |
| 6,184,984 | B1 | | 2/2001 | Lee et al. |

(Continued)

FOREIGN PATENT DOCUMENTS

GB    2173608 A    10/1986

(Continued)

Primary Examiner—Scott J Sugarman
(74) Attorney, Agent, or Firm—Browdy and Neimark, P.L.L.C.

(57) ABSTRACT

A lens arrangement is presented. The lens arrangement comprises a first element having a concave reflective surface and defining an optical axis of the lens arrangement, and a second substantially flat and at least partially reflective element spaced-apart from the first element along the optical axis. The second element is configured to allow light passage therethrough and is oriented with respect to the optical axis and the first element such that at a predetermined angle of incidence of an input light beam onto the second element, the input light beam is reflected onto the reflective surface of the first element and reflected therefrom to pass through the second element.

20 Claims, 13 Drawing Sheets

U.S. PATENT DOCUMENTS

| | | |
|---|---|---|
| 6,583,877 B2 | 6/2003 | Norton |
| 6,600,552 B2 | 7/2003 | Dinger |
| 6,728,043 B2 | 4/2004 | Gruner et al. |
| 7,019,918 B2 | 3/2006 | Wallerstein et al. |
| 2003/0020912 A1 | 1/2003 | Norton |

FOREIGN PATENT DOCUMENTS

| | | |
|---|---|---|
| WO | 2004010224 | 1/2004 |
| WO | 2005119225 A1 | 12/2005 |

* cited by examiner (GENERAL ART)

REFLECTIVE OPTICAL SYSTEM

FIELD OF THE INVENTION

This invention relates to a reflective optical system for use in measuring/inspection systems.

BACKGROUND OF THE INVENTION

Various types of optical systems utilize reflective objectives. These systems include for example, telescopes, UV microscopes, measurement systems operating in UV spectral range, etc.

The commonly used reflective objective is the Schwarzschild-type objective. As illustrated in FIG. 1, this objective includes a first apertured spherical mirror $M_1$ and a second spherical mirror $M_2$ accommodated in a spaced-apart relationship along an axis of symmetry of the mirrors. The second mirror $M_2$ is typically mounted on a so-called spider (shown schematically), which complicates the construction. Moreover this configuration suffers from diffractive effects that might occur on the spider, obscuration caused by the mirror $M_2$ and spider which results in about 20% aperture reduction, relatively high-angle reflection which causes polarization distortion, a high minimal numerical aperture (about 0.3) with significant angular obscuration near the optical axis.

Various imaging/measurement techniques require operation with a broad spectrum, i.e., from infra-red (IR) to deep ultraviolet (DUV). In this connection, refractive optics, due to limited availability of transparent materials at short wavelengths, cannot be used in a spectral range down to 190 nm. Moreover, refractive optics, due to unavoidable dispersion effects, causes high chromatic aberrations and thus does not enable illumination of a small spot needed for measuring in small measurement sites.

SUMMARY OF THE INVENTION

There is a need in the art to facilitate measuring/inspecting articles by providing a reflective optical system operable as an objective lens arrangement within a broad spectral range, from DUV or Vacuum UV (VUV) to NIR or IR.

According to one broad aspect of the invention, there is provided a lens arrangement comprising: a first element having a concave reflective surface and defining an optical axis of the lens arrangement, and a second substantially flat and at least partially reflective element spaced-apart from the first element along the optical axis, the second element being configured to allow light passage therethrough and being oriented with respect to the optical axis and the first element such that at a predetermined angle of incidence of an input light beam onto the second element, the input light beam is reflected onto the reflective surface of the first element and reflected therefrom to pass through the second element.

It should be noted that the first element having a concave surface may be configured as spherical, aspherical or parabolic type element.

According to one embodiment, the second element is an apertured mirror. This apertured mirror is accommodated such that the optical axis passes through the aperture, and at the predetermined angle of incidence of the input light beam onto the reflective surface of the second element, the beam is reflected onto the reflective surface of the first element and reflected therefrom to pass through the aperture in the second element.

Preferably, a lower surface of the apertured mirror (outer surface with respect to the first element) and its inner surface defined by the aperture are substantially anti-reflective, more preferably are substantially light absorbing. Preferably, the aperture in the second element has a substantially conical geometry with a cone base being at a lower surface of the second element.

According to another embodiment, the second element is a beam splitter. In this case, a shielding element is preferably provided configured so as to define a non-opaque region surrounded by opaque region of the shielding element. The shielding element is accommodated such that the optical axis passes through the non-opaque region. The shielding element may be implemented as an opaque coating on the surface region of the beam splitter defining the non-opaque region surrounded by the opaque coating.

The second element is positioned with respect to the optical axis so as to be inclined to the optical axis. The inclination angle is about 70-80 degrees, preferably about 79 degrees.

The reflective system of the present invention may be both in finite and infinite system configuration. For a finite conjugate configuration the second element is preferably accommodated in a back focal plane of the first element.

According to another broad aspect of the invention, there is provided a lens arrangement comprising: a first element having a concave reflective surface and defining an optical axis of the lens arrangement, and a second substantially flat element spaced-apart from the first element along the optical axis, the second element being configured as an apertured mirror and being oriented with respect to the optical axis and the first element such that the optical axis passes through the aperture and such that at a predetermined angle of incidence of an input light beam onto the mirror surface of the second element, the input light beam is reflected onto the reflective surface of the first element and reflected therefrom towards the aperture in the second element.

According to yet another broad aspect of the invention, there is provided a lens arrangement comprising: a first element having a concave reflective surface and defining an optical axis of the lens arrangement, and a second substantially flat element spaced-apart from the first element along the optical axis, the second element being configured as an apertured mirror, an outer surface of the second element and its inner surface defined by the aperture being substantially anti-reflective, the second element being oriented with respect to the optical axis and the first element such that the optical axis passes through the aperture and such that at a predetermined angle of incidence of an input light beam onto the mirror surface of the second element, the input light beam is reflected onto the reflective surface of the first element and reflected therefrom towards the aperture in the second element.

According to yet another broad aspect of the invention, there is provided a lens arrangement comprising: a first element having a concave reflective surface and defining an optical axis of the lens arrangement, and a second substantially flat element spaced-apart from the first element along the optical axis, the second element being configured as an apertured mirror, an outer surface of the second element and its inner surface defined by the aperture are substantially light absorbing, the second element being oriented with respect to the optical axis and the first element such that the optical axis passes through the aperture and such that at a predetermined angle of incidence of an input light beam onto the mirror surface of the second element, the input light beam is reflected onto the reflective surface of the first element and reflected therefrom towards the aperture in the second element.

According to yet another aspect of the invention, there is provided an optical system comprising an illuminator arrangement defining a first aperture stop of the system; a first element having a concave reflective surface and defining an optical axis of light propagation; and a second substantially flat and at least partially reflective element spaced-apart from the first element along the optical axis, the second element being configured to allow light passage therethrough and being oriented with respect to the optical axis and the first element such that at a predetermined angle of incidence of an input light beam onto the second element, the input light beam is reflected onto the reflective surface of the first element and reflected therefrom to pass through the second element, said second element and said first aperture stop defined by the illuminator arrangement being located in conjugate planes.

The system preferably comprises an optical polarizer assembly for directing illuminating light towards an article under measurements and collecting light returned from the article. Preferably, the polarizer assembly is mounted for rotation to vary an orientation of its preferred plane of polarization. The polarizer assembly comprises a polarizer element and preferably also a compensator element. The compensator element is configured for shifting a beam propagation axis towards an axis of rotation of the polarizer unit to thereby compensate for a shift of the beam propagation axis from the axis of rotation caused by the rotation of the polarizer unit. Such a compensator may be a plane parallel plate. The compensator is spaced-apart from the polarizer element, being located upstream or downstream thereof, with respect to a direction of propagation of illuminating light towards the article under measurements.

The illuminator arrangement may include first and second light sources, and a light directing arrangement. The light directing arrangement is configured to combine first and second light portions produced by the first and second light sources, respectively, and direct combined light towards the article under measurements. The first and second light sources may be configured to produce the first and second light portions of different wavelength ranges, respectively.

Preferably, the illuminator arrangement includes an aperture accommodated in the optical path of the combined light. This aperture and the second element are located in conjugate planes. The illuminator arrangement may include reflective relay optics. The aperture of the illuminator is preferably of a double-aperture configuration having a central blocking region.

According to yet another aspect of the invention, there is provided a polarizer unit comprising a polarizer and a compensator accommodated in a spaced-apart relationship along an axis, the compensator being configured so as to, when being rotated together with the polarizer about said axis, shifting a light beam propagation axis towards said axis of rotation.

According to yet another aspect of the invention, there is provided an optical system comprising an illuminator arrangement and an objective lens arrangement; the illuminator arrangement comprising a light source assembly and an aperture assembly; the objective lens arrangement comprising a first element having a concave reflective surface and defining an optical axis of the lens arrangement, and a second at least partially reflective element spaced apart from the first element along the optical axis, the second element being configured to allow light passage therethrough and being oriented with respect to the optical axis and with respect to the first element such that at a predetermined angle of incidence of an input light beam onto the reflective surface of the second element, the input beam is reflected onto the reflective surface of the first element and reflected therefrom to pass through the second element, said aperture of the illuminator arrangement and said second element being located in conjugate planes.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
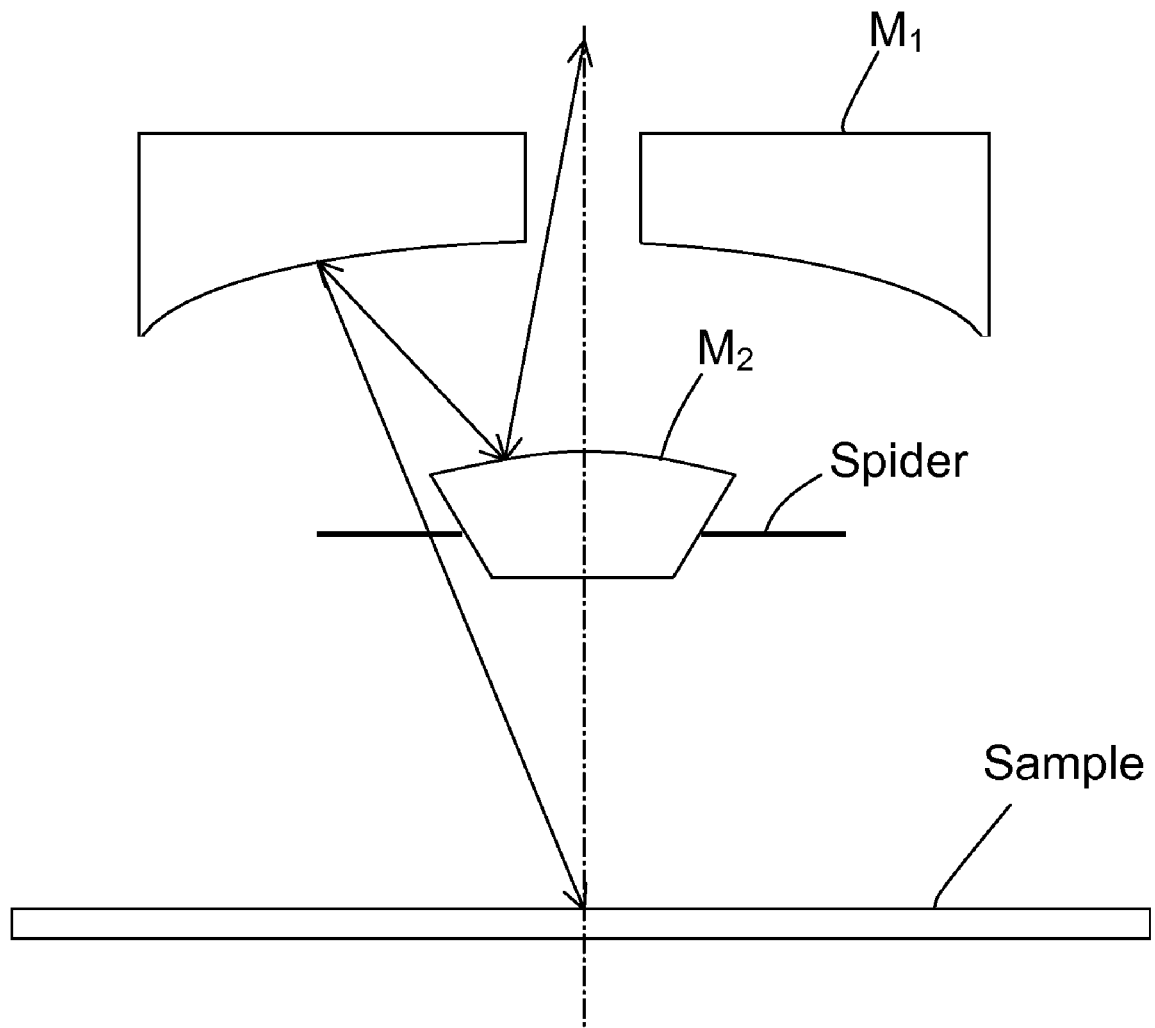
FIG. 1 shows the commonly used Schwarzschild-type reflective objective.

FIG. 1 shows the commonly used Schwarzschold-type reflective objective, including the first apertured spherical mirror Ml and the second spherical mirror $M_2$ mounted on a spider and accommodated in a spaced-apart relationship along an axis of symmetry of the mirrors.

Figure 2A:
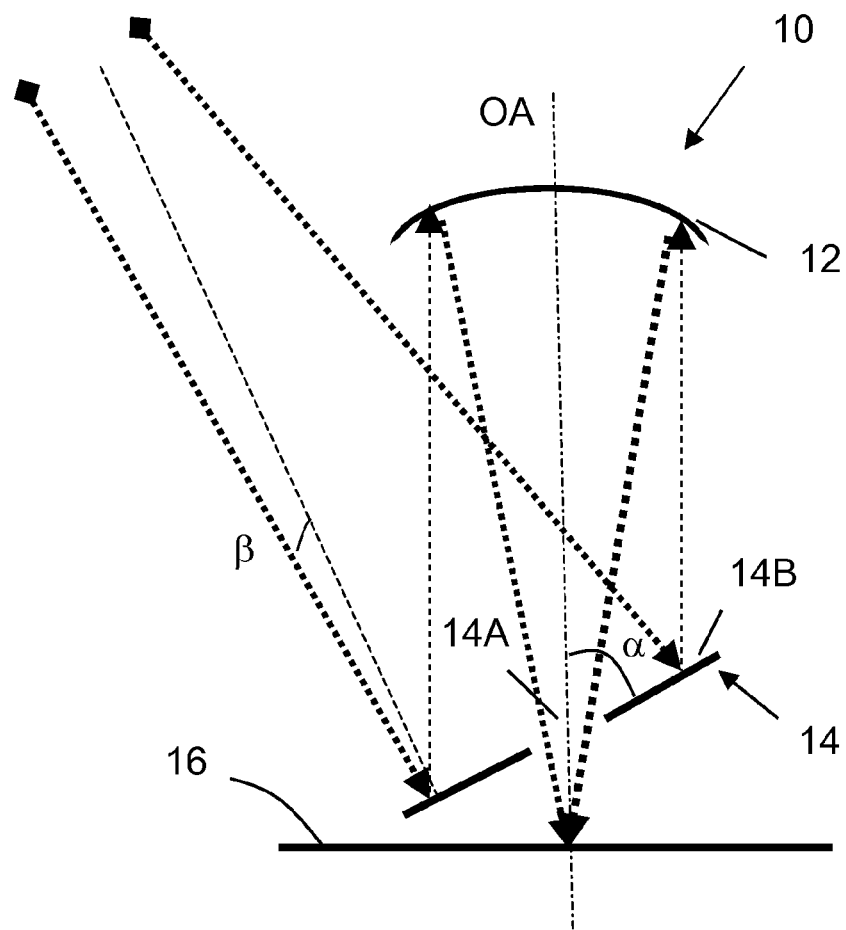
FIG. 2A schematically illustrates an example of a lens arrangement according to the invention.

Referring to FIG. 2A, there is schematically illustrated an example of a lens arrangement 10 according to the invention. The lens arrangement 10 is configured as a reflective objective system and is suitable for use in measuring/inspecting articles, particularly patterned articles, such as semiconductor wafers. The system 10 is configured for operating with a broadband spectrum, namely from Vacuum UV (VUV) and/ or Deep UV (DUV) up to Infrared (IR), e.g. within 190-950 nm, and is also operable with polarized light in this broad spectrum practically without a change of the polarization state.

The system 10 includes a concave mirror 12 (constituting a first reflective element) which may be of spherical, aspherical or parabolic type, and a substantially flat partially reflecting element 14 (constituting a second reflective element). In the present example, the element 14 is in the form of a mirror having an aperture 14A surrounded by reflective upper surface 14B of mirror 14, e.g., is an annular mirror. For a small field of view (FOV) system, the use of a spherical type mirror 12 is preferable since it is simple, cheap and enables high quality surface treatment. For a large FOV application, a parabolic mirror is preferable as enabling better compensation for aberrations.

In the examples described herein, a spherical-type mirror 12 is considered, but it should be understood that the present invention is not limited to this specific configuration.

The element 12 and 14 are arranged in a spaced-apart relationship along an optical axis OA of the system. The second element 14 is positioned with respect to the optical axis OA and to the first element 12 such that at a predetermined angle of incidence of an input light beam onto the element 14, the beam is reflected therefrom to the reflective surface of the first element 12 and is reflected therefrom to pass through the aperture 14A of the second element 14. In the present example, the mirrors 12 and 14 are accommodated such that they face each other by their reflective surfaces, optical axis OA passes through the center of the aperture 14A, and mirror 14 is located between the spherical mirror 12 and article 16 under measurements. When in operation, all light paths are essentially symmetric about the optical axis on the article under measurement/inspection. Thus, the system 10 is the so-called "on-axis" objective system.

An input light (light used for illuminating the article 16), when entering the system 10, first impinges onto the at least partially reflective element 14, i.e., on the reflective surface 14B of the annular mirror 14 in the present example, and is reflected therefrom to the inner surface of the spherical mirror 12, which reflects the light to focus it onto the article 16 via the aperture 14A. It is assumed that the article 16 is located accurately in the focal plane of the mirror 12. The second element 14 (e.g., annular mirror) is oriented with respect to the optical axis OA at a certain inclination angle $\alpha$ selected so as to ensure desired small angle of incidence $\beta$ of the input light, reflected from mirror 14, onto mirror 12. Angle $\alpha$ preferably ranges from 70 to 80 degrees, most preferably is about 79 degrees. Angle $\beta$ is essentially (90-$\alpha$). Light reflected from the article is collected through the aperture 14A and propagates to the spherical mirror 12, which reflects this light onto the surface 14B of the annular mirror, which due to its tilted orientation reflects the light out of the system 10. The spherical mirror 12 is preferably manufactured so as to prevent or at least significantly reduce scattering of light from this mirror, which is more problematic at short-wavelengths, thereby reducing detrimental chromatic effects. Due to small angles of reflection from the spherical mirror 12, it practically does not affect the polarization of light within the entire broadband spectrum.

Figure 2B:
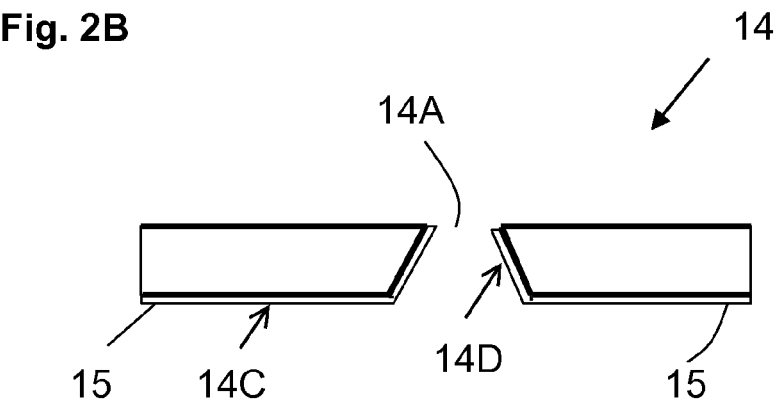
FIG. 2B more specifically illustrates the configuration of an apertured mirror suitable to be used in the lens arrangement of the present invention.

FIG. 2B more specifically illustrates the configuration (cross-section) of mirror 14. The outer lower surface 14C and the inner surface 14D of the mirror defined by the aperture are preferably substantially light absorbing. This is implemented by providing on these surfaces a specific coating 15 such as a black paint. As also shown in the figure, the inner surface 14D of aperture 14A has a substantially conical geometry with the cone base being located at the bottom side of the mirror 14. This configuration provides for eliminating or at least substantially reducing edge effects in collected light returned (reflected) from the article.

Figure 2C:
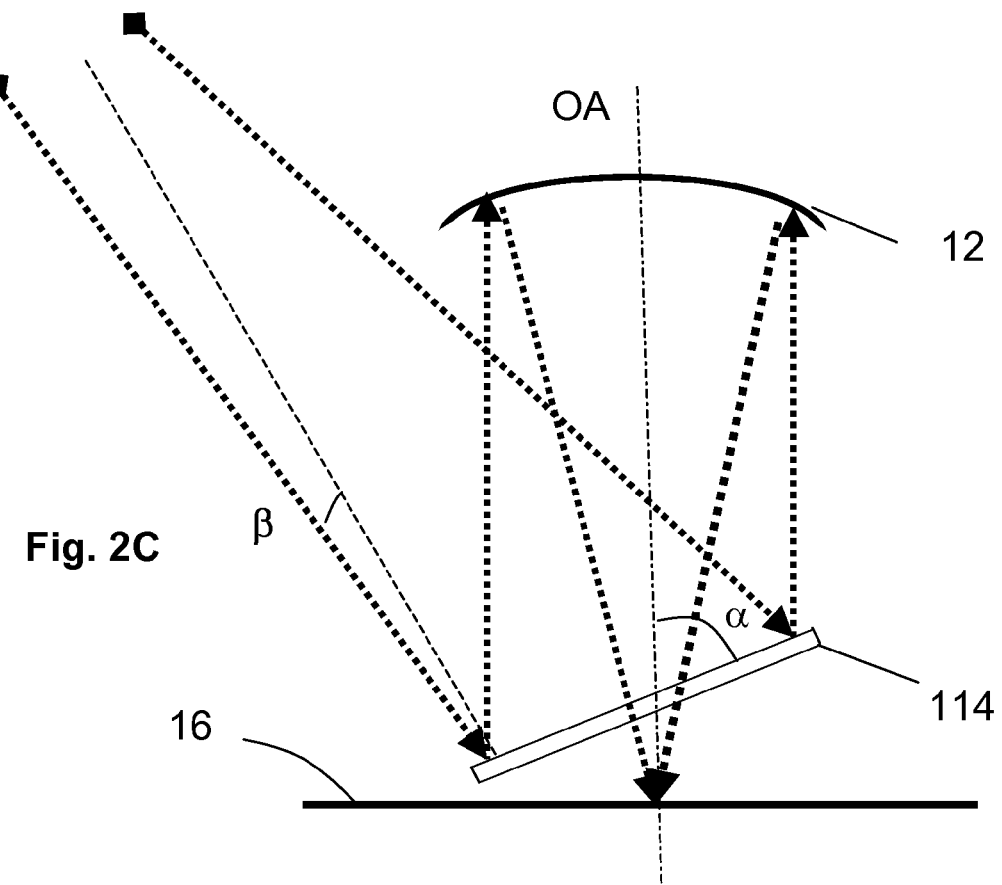
FIGS. 2C and 2D schematically illustrate two more examples, respectively, of a lens arrangement according to the invention.
Figure 2D:
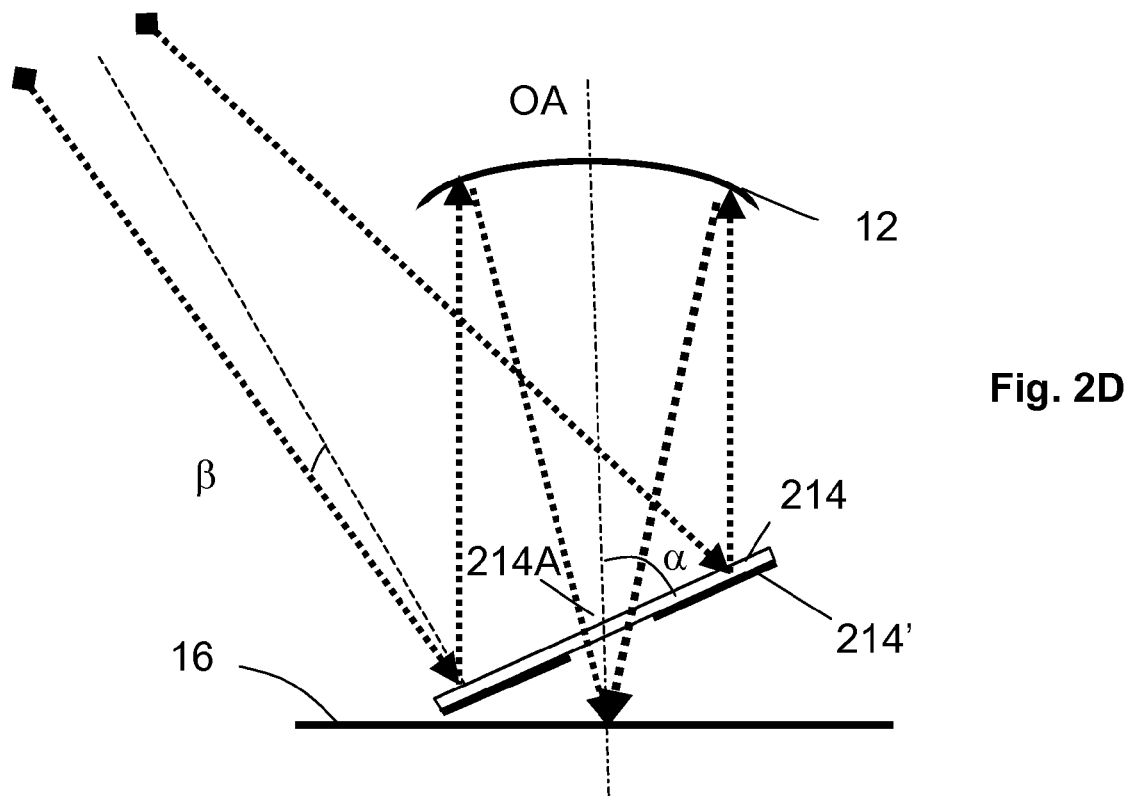

It should be noted that the annular mirror 14 may be replaced by a plate beam splitter with a coating optimized for a wavelength range. This is illustrated in FIG. 2C, showing a reflective objective lens arrangement including a spherical mirror 12 (constituting a first reflective element) and a beam splitter 114 (constituting a second reflective element). In this case, there is no angular "hole" in the incident beam caused by aperture (14A in FIG. 2A). However, the energy loss caused by the beam splitter 114 (about 75%) might reduce a signal-to-noise ratio of the system. This energy reduction may be compensated by increasing a measurement time. In the configuration of FIG. 2C, light propagating through the beam splitter might undesirably increase parasitic scattering effects in the system. This can be avoided by using opaque shielding. This is illustrated in FIG. 2D, showing a reflective objective lens arrangement including a spherical mirror 12 and a beam splitter 214 having an opaque coating 214' defining an uncoated region 214A (functioning as an aperture). In the present example, an opaque shielding element is implemented as a coating on the beam splitter, but it should be understood that the same may be achieved by using a separate element (mask) located close to the beam splitter. The opaque shielding element blocks light impinging thereon within all the regions outside the aperture-region (i.e., transparent region).

Figure 3:
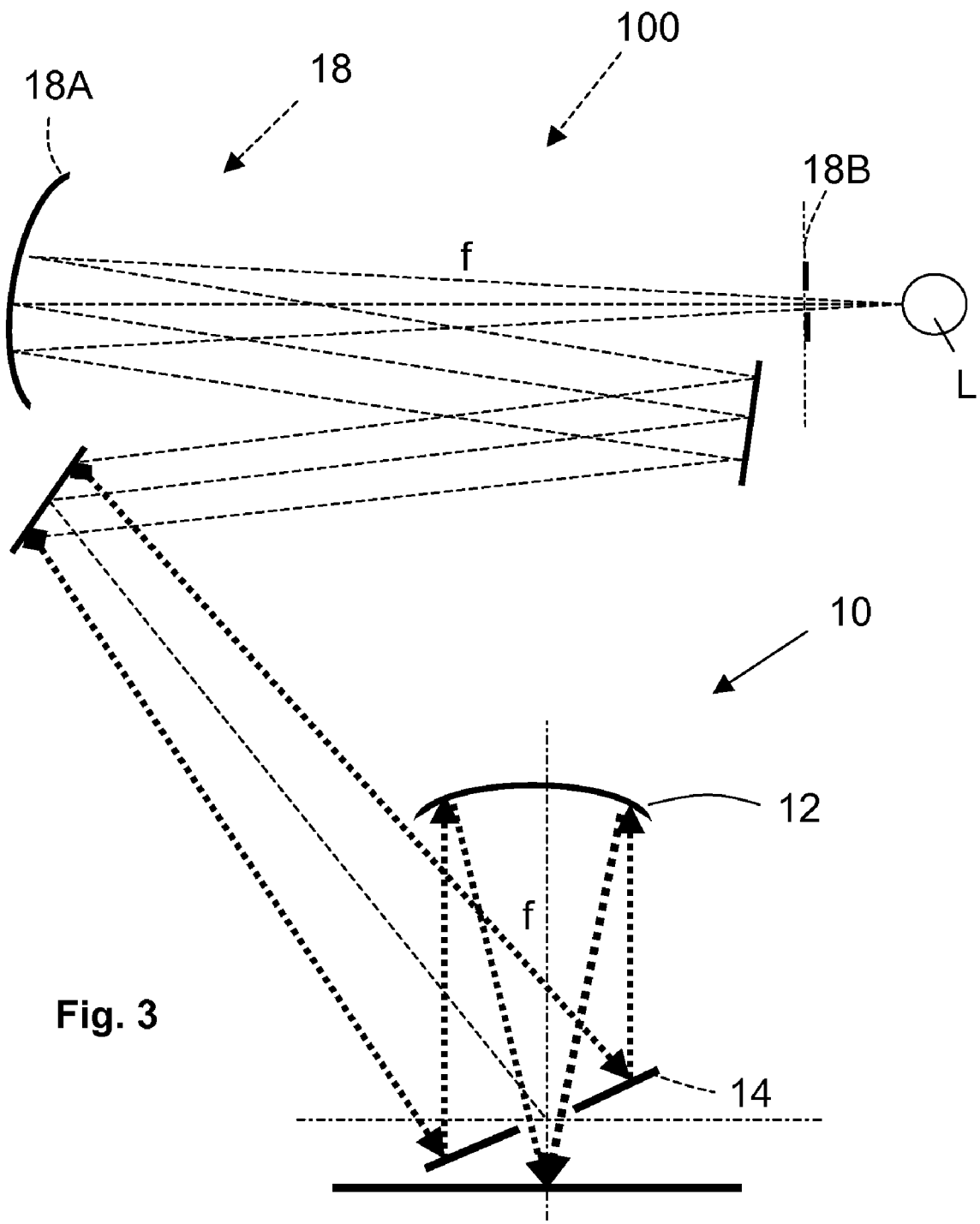
FIG. 3 illustrates a telecentric optical system utilizing the lens arrangement of the present invention.

Reference is made to FIG. 3 showing how the lens arrangement 10 can be used in a telecentric optical system 100. The system 100 includes an optical lens arrangement 18 of an illuminator and the objective lens arrangement 10. The illuminating lens arrangement 18 includes a relay lens 18A (preferably a spherical mirror), and an aperture 18B located near a focal plane of the relay lens (spherical mirror) 18A. The aperture 18B of the illuminator is located at a position such that the relay lens (spherical mirror) 18A preferably images the aperture 18B to the back focal plane of the objective lens (spherical mirror) 12, i.e., adjacent to the mirror 14. It should be noted that the lens arrangement of the present invention can be used both with finite conjugate imaging and infinite conjugate imaging that include a tube lens as well. Additionally, folding mirrors 19A and 19B or other beam directing assemblies may be used in order to provide a desired configuration (size, light propagation direction, etc.) of the optical system 100.

Figure 4:
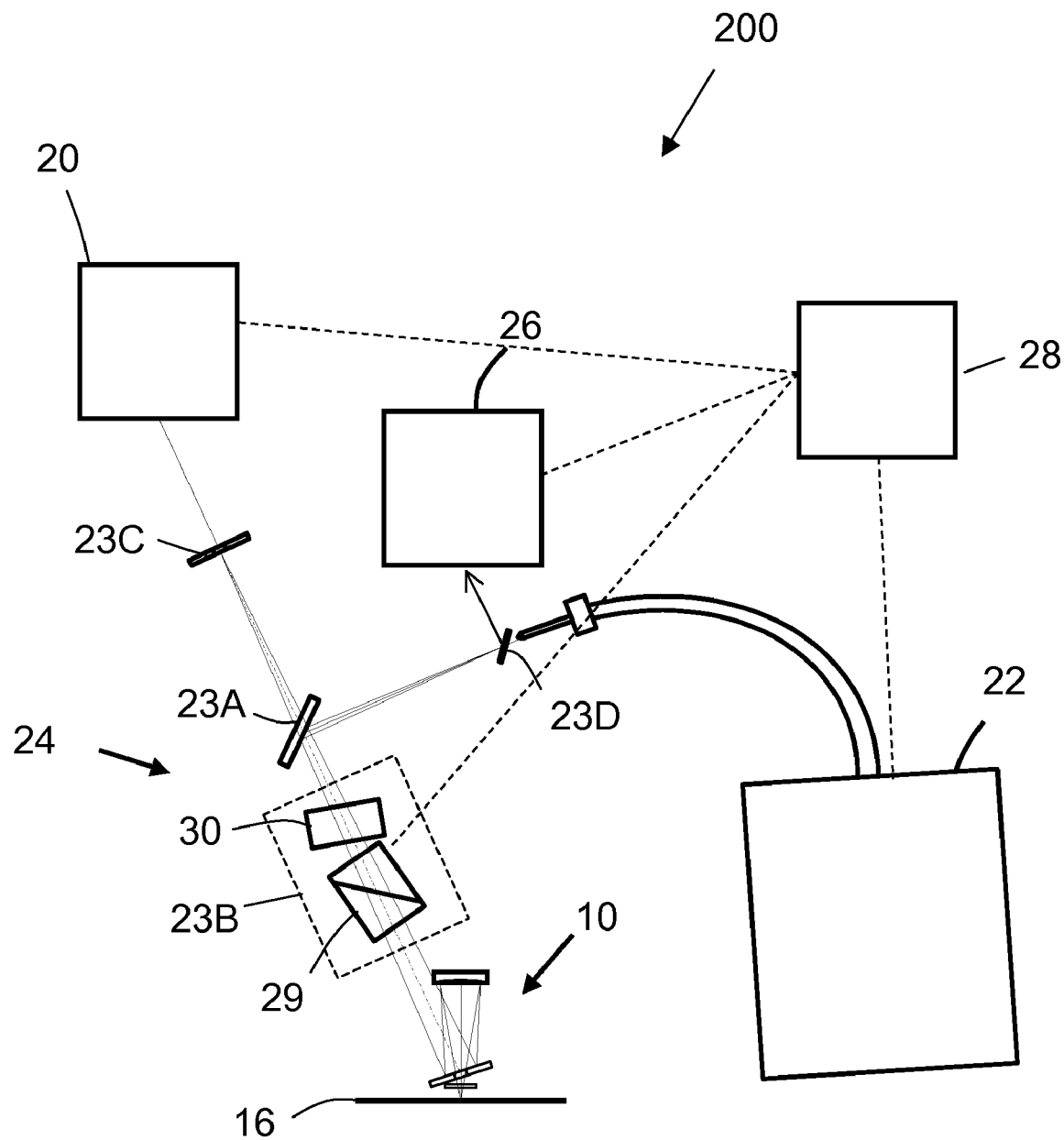
FIG. 4 schematically illustrates a measurement system of the present invention.

FIG. 4 schematically illustrates an optical measurement system 200 utilizing the reflective objective system 10 of the present invention. The system 200 includes an illuminator arrangement 20; a spectrometer-type detection unit 22; and a light directing unit 24 configured for focusing incident light onto an article under measurement/inspection and collecting light from the article to the detection unit. The system 200 preferably also includes an imaging system 26. Further provided in the measurement system 200 is a control system 28 connectable to various elements of system 200 for controlling their operation and processing measured data.

The illuminator arrangement 20 is configured for producing broadband illumination, which for the purposes of the present invention (inspection/measurements in patterned articles) is of about 190-950 nm. Various configurations of the illuminator arrangement will be described further below.

The light directing unit 24 includes a beam splitter/combiner 23A; an optical polarizer unit 23B; and a reflective objective arrangement 10. Also preferably provided in the unit 24 is an aperture 23C serving as a field stop. Considering the use of an imaging system, the light directing unit 24 also includes a beam separator such as a pinhole mirror 23D accommodated in the optical path of light returned from the article in order to transmit a part of light impinging on the pinhole to the spectrometer 22 and reflect the other part of this light to the imaging system 26. It should be understood that such a beam separation may also be implemented by replacing the pinhole mirror by a standard beam splitter. An example of the imaging system 26 will be described further below with reference to FIG. 14.

The optical polarizer unit 23B includes a polarizer element 29 and a compensator element 30. The polarizer unit 23B is operated by the control unit 28 so as to provide a desired polarization of light.

Figure 5:
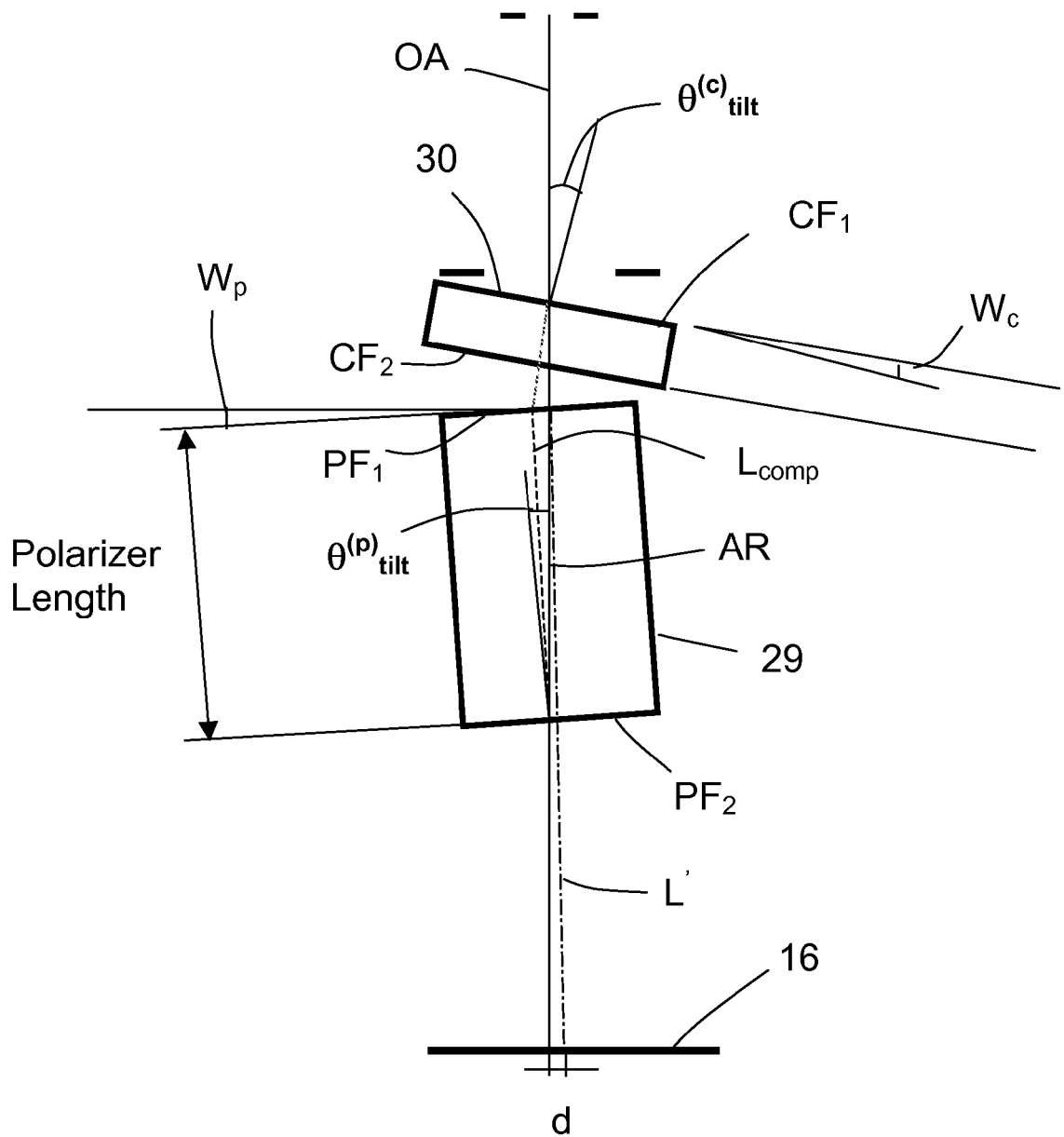
FIG. 5 more illustrates the principles of a compensator element in a polarizer unit used in the system of the present invention.

As shown more specifically in FIG. 5, the provision of the compensator 30 is associated with the following. In order to prevent undesired effects (ghost) caused by reflections from the facets of the polarizer, the polarizer is tilted in relation to the optical axis OA of the system at a small angle $\theta^{(p)}_{tilt}$ (e.g., of about 2.5°). Due to manufacturing tolerances, polarizer's facets $PF_1$ and $PF_2$ are not substantially parallel, forming a small optical wedge (about 1') which is schematically shown as an angle $W_p$. Rotation of the polarizer practically causes a shift of the light beam L' from the axis of rotation AR of the polarizer (which is substantially coinciding with the optical axis OA of the system), which will result in a shift d of the illuminated spot on the article (e.g., wafer). In order to compensate for such a shifting, the compensator 30 configured like an optical wedge is used, where the outer facet $CF_1$ of the compensator 30 forms an angle $W_c$ (of about 1') with respect to the opposite facet $CF_2$, and the compensator 30 is tilted a small angle $\theta^{(c)}_{tilt}$ (e.g., of about 8°) in relation to the optical axis OA. In that case, a light beam propagates along a "folded" path $L_{comp}$ and an illuminated spot on the article is not shifted relative to the axis of polarizer rotation AR. During assembling the polarizer unit 23B, the compensator element 30 and the polarizer element 29 are rotated with respect to each other in order to compensate the effects of polarizer tilt tolerances, and/or polarizer optical wedge, and/or polarizer length tolerances, by providing the appropriate orientation of the polarizer and compensator wedges.

Figure 6:
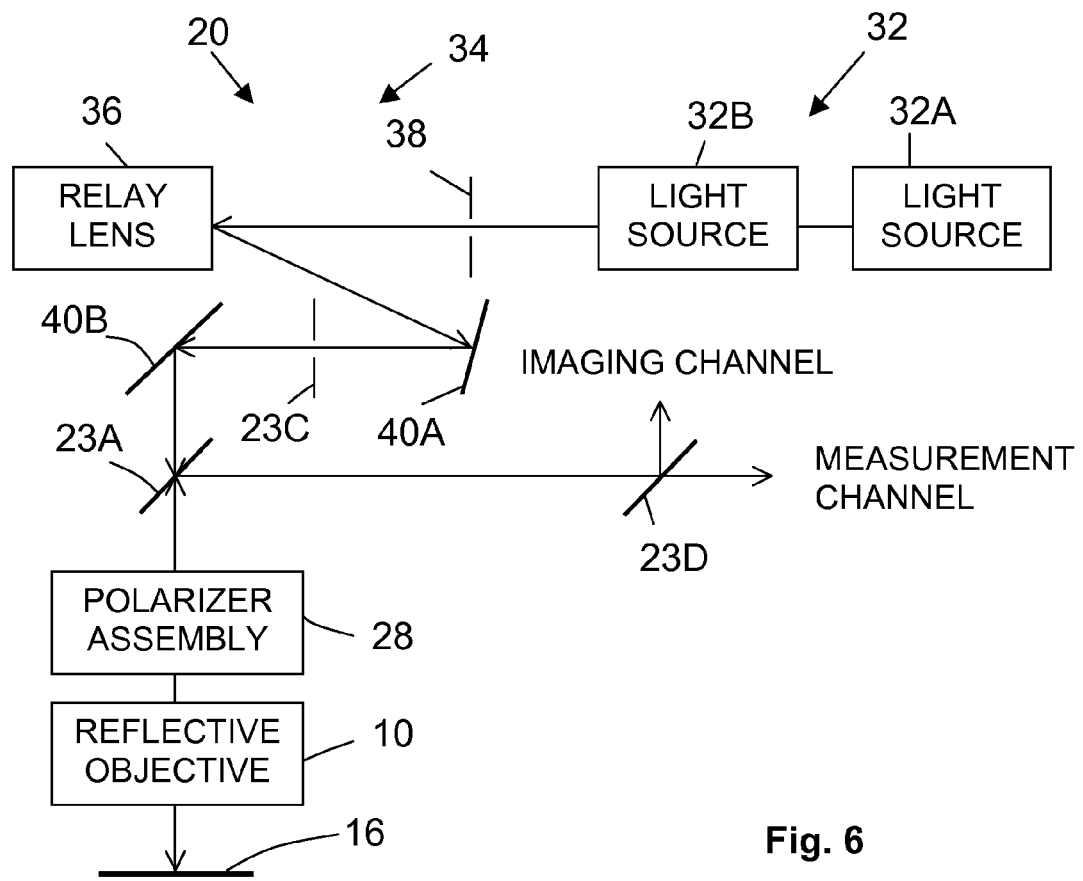
FIG. 6 illustrates one example of an illuminator arrangement suitable to be used in the system of the present invention.

Reference is made to FIG. 6 exemplifying the configuration of the illuminator arrangement 20. In the present example, the illuminator arrangement 20 includes a light source assembly, generally at 32, and a light directing assembly 34. The light source assembly 32 includes a first light source 32A capable of producing a first light portion including a visual spectral range, e.g., Xe-lamp or QTH lamp; and a second light source 32B capable of producing a second light portion including DUV (VUV) spectrum, e.g., Deuterium lamp. The first and second light sources are preferably selected such that the spectral ranges of the first and second light portions partially overlap so as to provide a desired intensity distribution over the required spectral range. An example of the spectral characteristics of light sources 32A and 32B will be described further below with reference to FIG. 12.

The light directing assembly 34 includes a reflective relay lens arrangement 36 which in the present example is constituted by a spherical mirror; an aperture 38 accommodated near the back focal plane of the relay lens arrangement 36; and includes optional folding mirrors 40A and 40B. The relay lens arrangement 36 directs light coming from the light source assembly (first and second light portions) to the first folding mirror 40A, which reflects the light to the second folding mirror 40B, which in turn directs the light towards the light directing unit (24 in FIG. 4), namely towards the beam splitter/combiner 23A. It should be understood that the provision of folding mirrors is optional. In the example of FIG. 6, the aperture 23C is located in the optical path of light propagating from mirror 40A to mirror 40B, but it should be noted that the aperture 23C may alternatively be located downstream of mirror 40B, namely at the output of the illuminator arrangement 20 as shown in FIG. 4.

Figure 7:
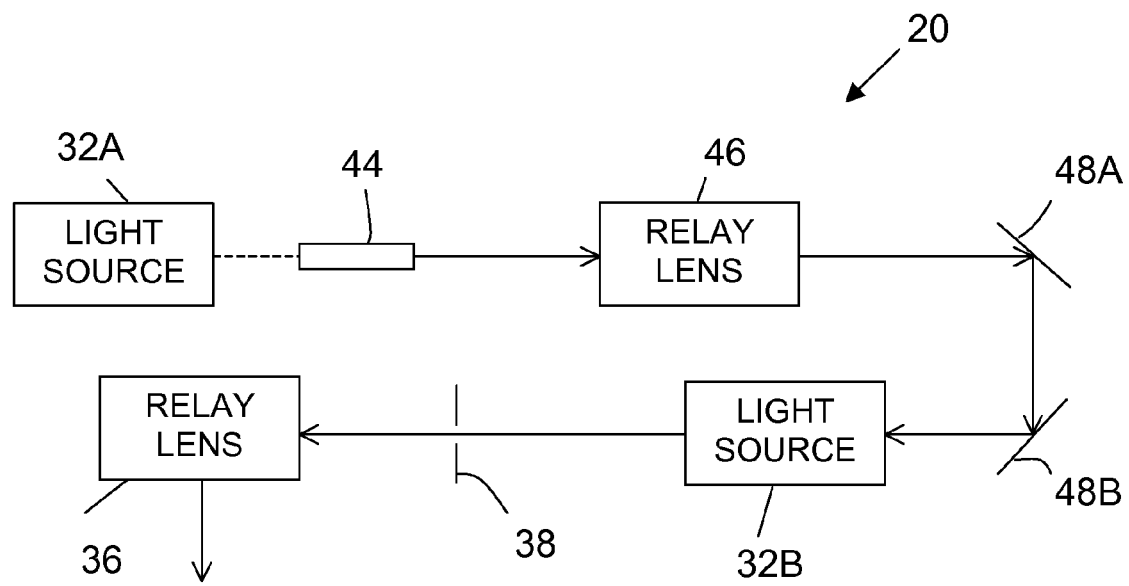
FIG. 7 illustrates another example of an illuminator arrangement suitable to be used in the system of the present invention.

FIG. 7 shows another example of combining illumination from two light sources 32A and 32B. As shown, light from lamp 32A is directed via an optical fiber 44 to a refractive relay lens arrangement 46, which directs this light towards the lamp 32B via folding mirrors 48A and 48B. Turning back to FIG. 6, it should be understood that using the light directing scheme of FIG. 7 in the illuminator arrangement 20, the element denoted 32A located proximate to lamp 32B upstream thereof would be constituted by the folding mirror 48B.

The aperture 38 of the illuminator arrangement (of either one of the examples herein described) is conjugate with the back focal plane of the reflective objective 10 and preferably also with the apertured second element (14 in FIG. 2).

Figure 8:
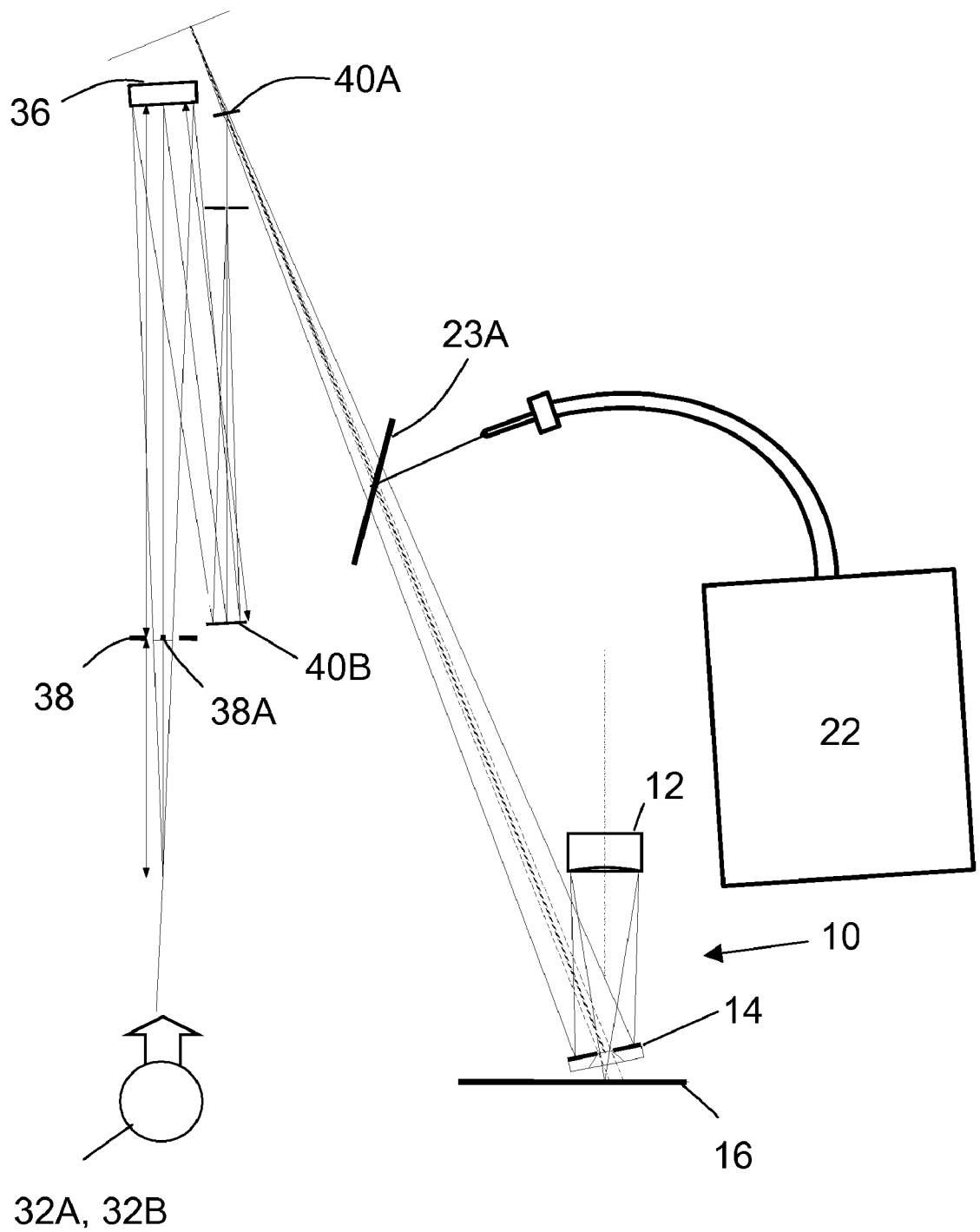
FIG. 8 illustrates the measurement system including the illuminator arrangement of the present invention.

For the preferred embodiment of the invention, where the reflective objective system utilizes an annular mirror 14, the aperture 38 is preferably formed with a central blocking region surrounded by the aperture gap, i.e., is the so-called double-aperture assembly. This is illustrated in FIG. 8, exemplifying the entire measurement system of the present invention. As shown, the aperture 38 has a central blocking region 38A, thus preventing illuminating light from being incident onto the opening 14A in the mirror 14, and allowing only the reflection of the illuminated light from the spherical mirror 12 to propagate towards the aperture 14A.

Figure 9:
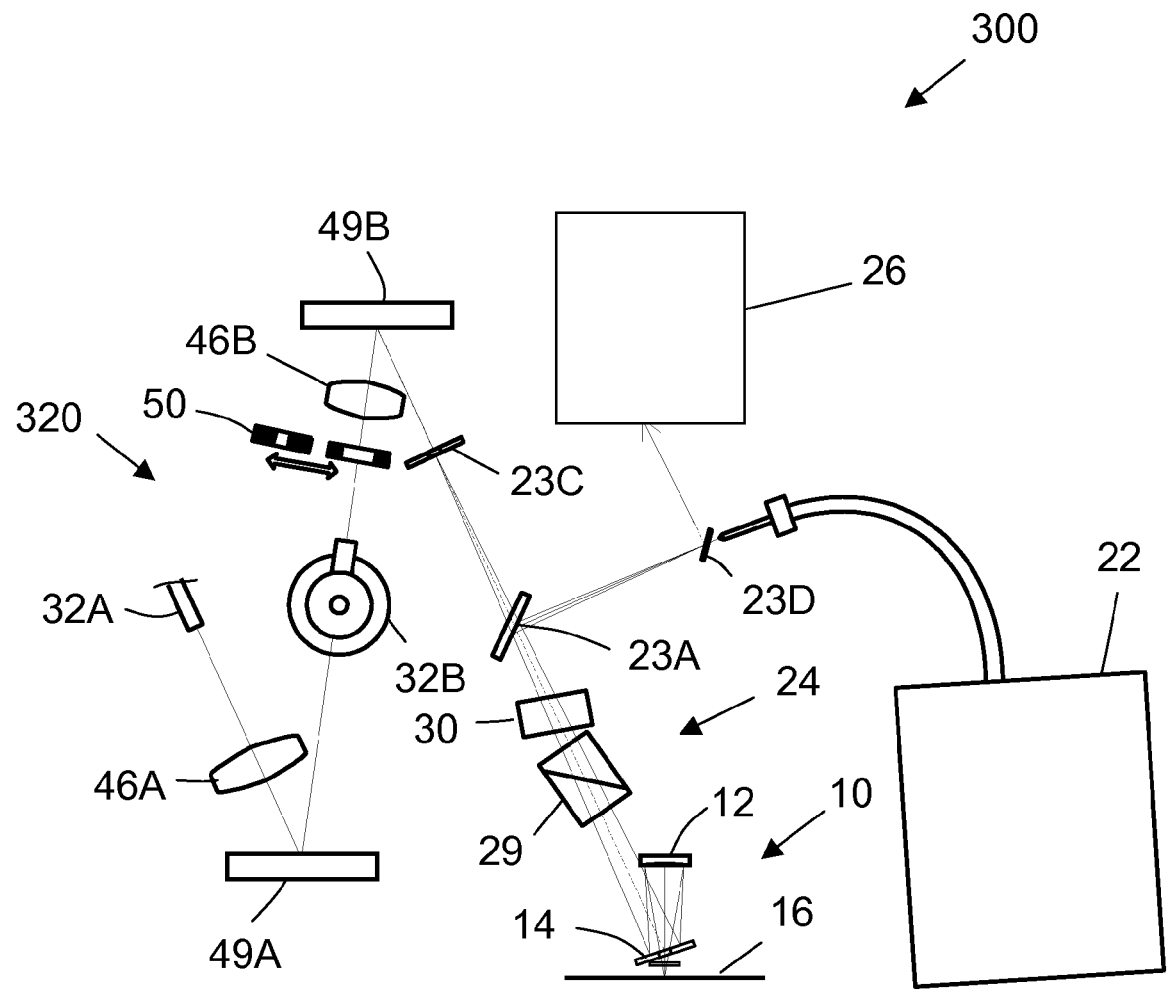
FIG. 9 illustrates a measurement system of the present invention utilizing yet another configuration of the illuminator arrangement.

Referring to FIG. 9, there is illustrated another example of a measurement system 300. To facilitate understanding, the same reference numbers are used in all the figures for identifying those components which are common in all the examples of the invention. The system 300 includes an illuminator arrangement 320; a spectrometer-type detection unit 22; a light directing unit 24; and preferably also includes an imaging system 26, in which case a beam separating element 23D (e.g., pinhole mirror) is appropriately provided to define imaging and measurement channels. In this example, the illuminator arrangement 320 includes two light sources 32A and 32B operating in different wavelength ranges as described above; and a light directing assembly 34 including a refractive relay lens 46A and folding mirror 49A directing the first light portion from lamp 32A to lamp 32B, another relay lens 46B and folding mirror 49B to direct the combined light from both sources, and an aperture assembly 50 with variable apertures of various diameters and shapes. As shown in the figure, system 300, similarly to system 200, is preferably equipped with a field stop aperture 23C.

Figure 10:
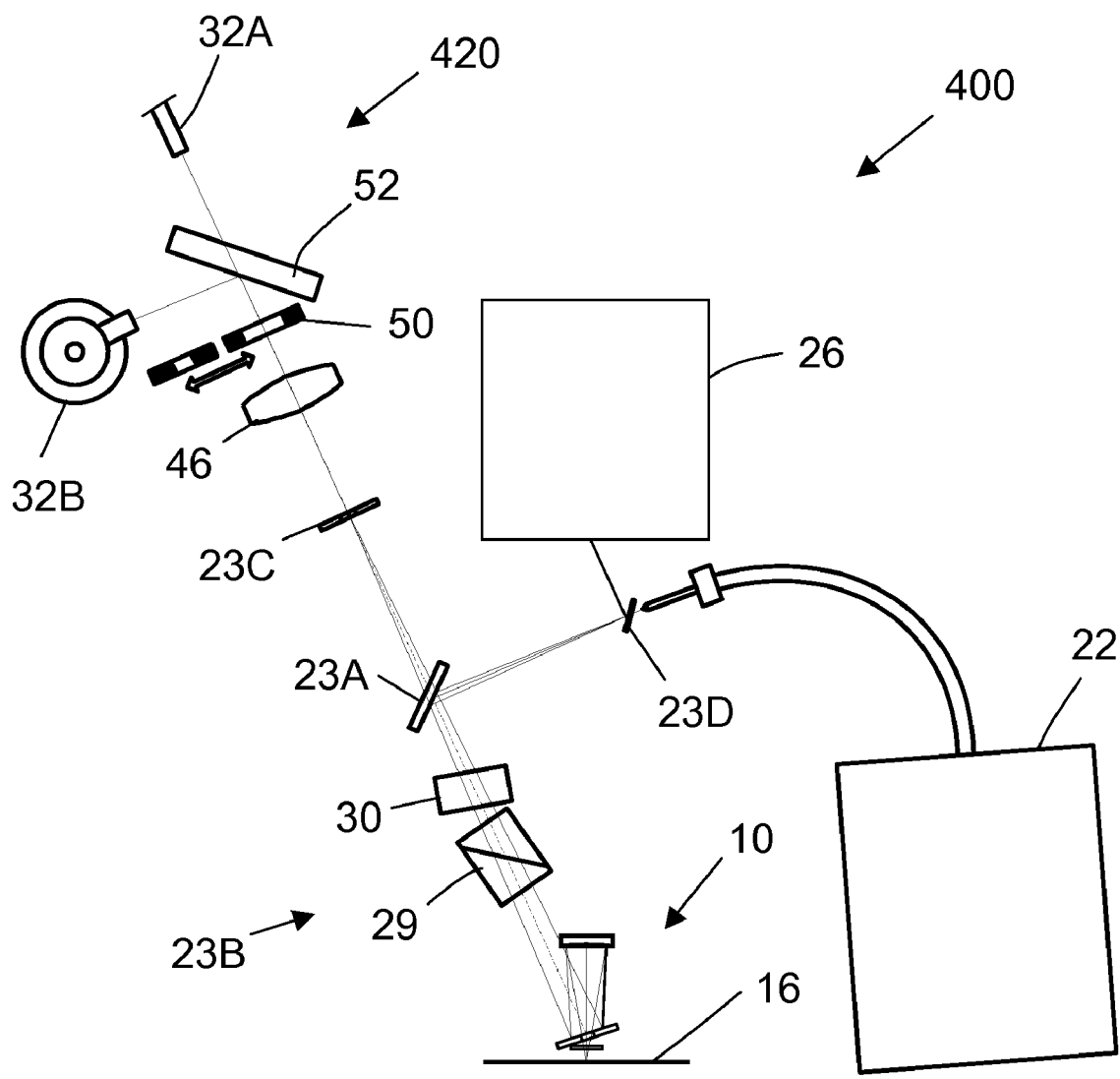
FIG. 10 illustrates a measurement system of the present invention utilizing yet another configuration of the illuminator arrangement.

FIG. 10 exemplifies yet another configuration of a measurement system 400. System 400 is generally similar to the previous examples, but distinguishes therefrom in the configuration of its illuminator arrangement 420. The latter includes different light sources 32A and 32B and a beam combiner 52 for combining the first and second light portions emitted by light sources 32A and 32B, respectively; and a relay lens 46.

Figure 11:
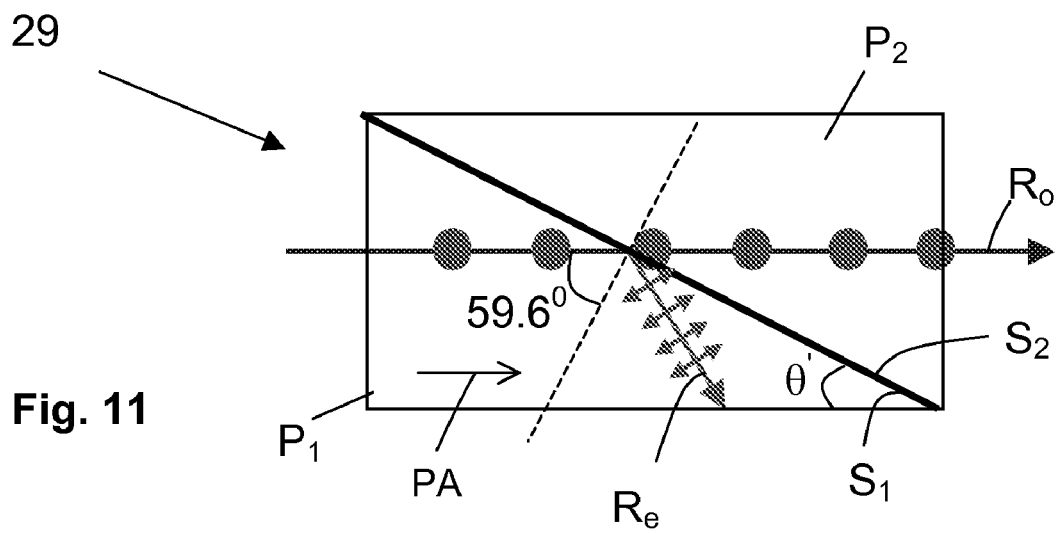
FIG. 11 exemplifies a configuration of a polarizer unit suitable to be used in the present invention.

Reference is now made to FIG. 11 schematically illustrating a preferred configuration of the polarizer 29 suitable to be used in the measurement system of the present invention. This polarizer is the subject of a co-pending application IL 160724, assigned to the assignee of the present application. The polarizer 29 is formed by two prisms $P_1$ and $P_2$ attached to each other by an optical glue layer GL between the tilted surfaces of $S_1$ and $S_2$ of the prisms $P_1$ and $P_2$, respectively. In this device, the following parameters are appropriately selected to ensure the device operation for light within the spectral range of about 190 nm-950 nm: cut angle θ' of the prism; and the properties of the glue material layer GL.

The prisms $P_1$ and $P_2$ are made of a birefringent material that is transparent for the required broadband spectral range, and is preferably α-BBO or quartz. The prisms are configured such that the preferred axis PA of the prism material forms a predetermined angle θ' (cut angle) with the tilted surface $S_1$ of the prism $P_1$ by which it is coupled to the other prism $P_2$. The glue material for the layer GL located between surfaces $S_1$ and $S_2$ is selected so as to be characterized by a dispersion profile $n_g(\lambda)$ matching the dispersion profiles $n_e(\lambda)$ and $n_o(\lambda)$ of the prism material for, respectively, extraordinary and ordinary rays $R_o$ and $R_e$ in the required spectral range. Moreover, the glue material is selected to be stable over time when exposed to variations in environmental conditions (temperature variations, UV radiation, etc.). For α-BBO crystal prisms, the preferred glue material is a Silicon RTV transparent to electromagnetic radiation ranging from 190 nm to 950 nm. Such glue may be CV15-2500, commercially available from NuSil Technology, USA. A 50 μm layer of this glue has about 95% transparency over the whole DUV to NIR spectrum.

Figure 12:
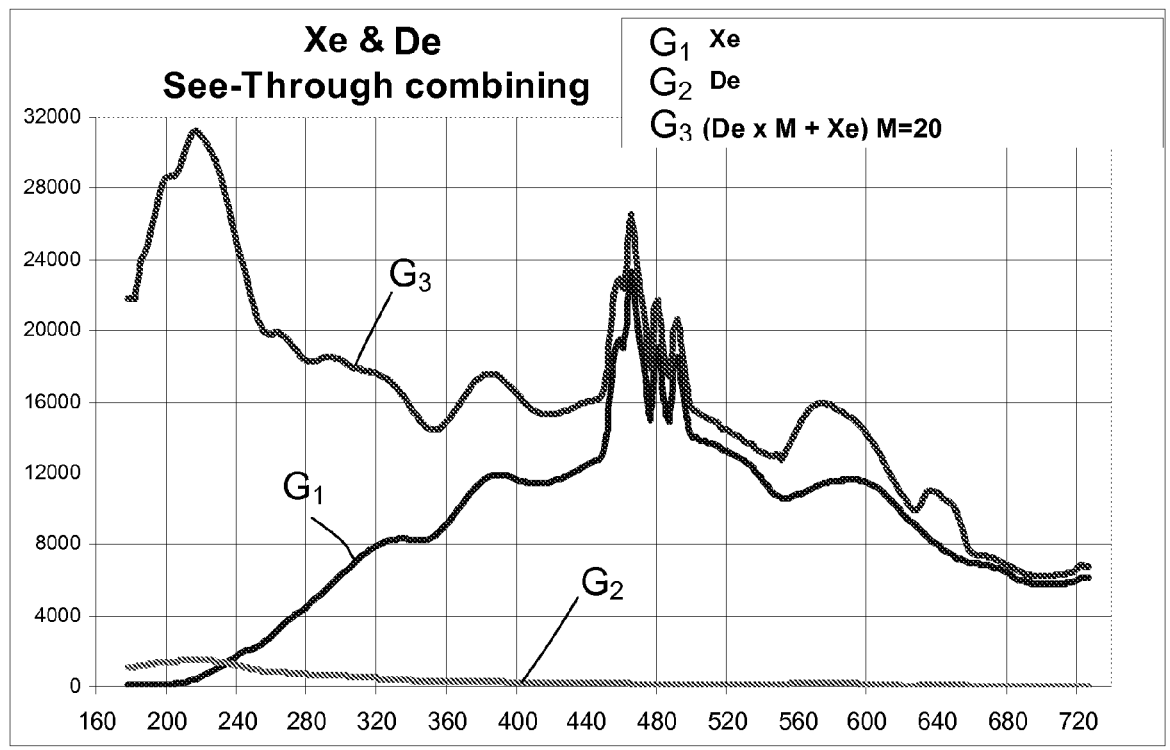
FIG. 12 illustrates the spectral characteristics of light sources suitable to be used in the present invention.

FIG. 12 exemplifies the spectral characteristics (intensity of emitted light as a function of wavelength) of light sources 32A and 32B. Three graphs $G_1$, $G_2$, $G_3$ are shown corresponding to the spectral characteristics of, respectively, Xe-lamp, Deuterium lamp, and the combined light from both lamps (Xe:De ratio is 1:20). Thus, the combined light includes the spectrum of two different lamps with sufficient intensity within the entire spectral range.

Figure 13:
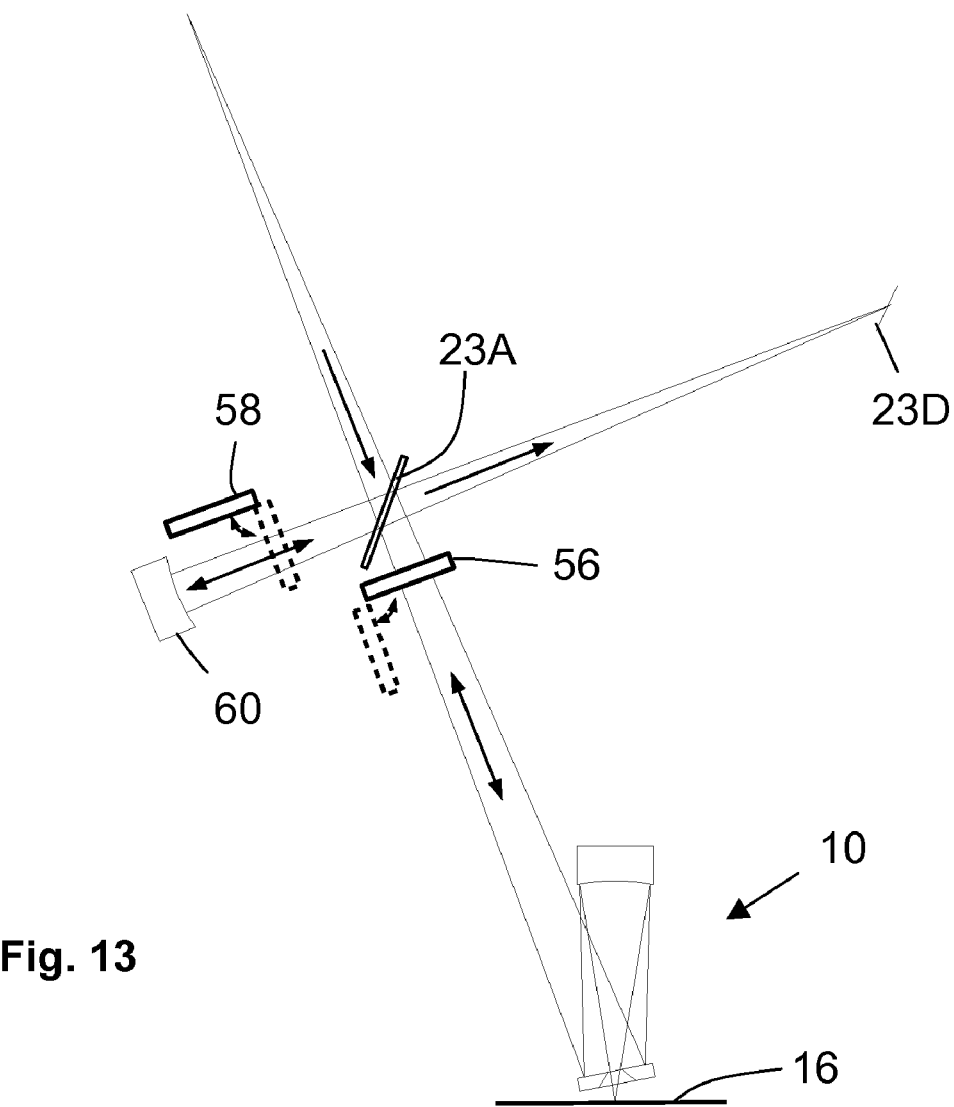
FIG. 13 schematically illustrates how the system of the present invention is switched between actual measurement mode and calibration mode.

FIG. 13 illustrates the main principles of another aspect of the invention consisting of monitoring the intensity of light produced by the entire light source assembly (two-lamp assembly). As shown, two controllable shutters 56 and 58 and a mirror 60 are provided so as to selectively allow and prevent the illuminating light propagation towards the article under measurement/imaging. In the actual measurement mode, shutter 56 is in its operable (opened) position and shutter 58 is inoperative (closed) as shown in the figure in dashed lines. Hence, the illuminating light propagates towards the article. In the monitoring mode, as shown in the figure, shutter 58 is operative (open) and shutter 56 is inoperative (closed), in which case the illuminating light is prevented from reaching the article while the portion of the illuminating light that is reflected by the beam splitter 23A is reflected by mirror 60 towards the pinhole 23D, i.e., towards measurement and imaging channels. This enables to monitor and calibrate the illuminating light parameters and thereby improve the measurement stability. It should be understood that shifting the shutter between its operative and inoperative positions may be achieved by any suitable mechanism, e.g., by mounting the shutter for rotation with respect to the optical path of light (as shown in the figure). The same control system (28 in FIG. 4) may be used for controlling the shutter operation.

Figure 14:
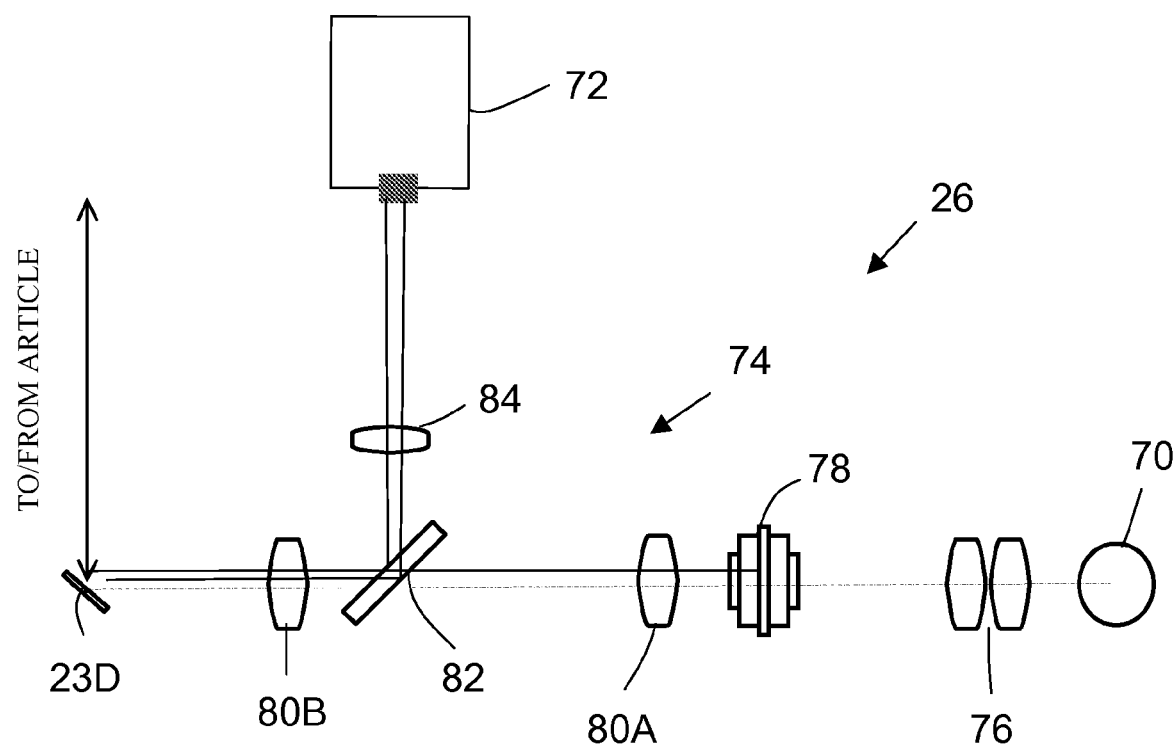
FIG. 14 schematically illustrates the configuration of an imaging system suitable to be used with the present invention.

FIG. 14 exemplifies the configuration of the imaging system 26 suitable to be used in the present invention. Generally, the imaging system is configured to acquire images of the article and to implement autofocusing. The imaging system 26 includes a light source assembly 70, detection unit 72 and a light directing system 74. The latter includes a condenser lens assembly 76 (two-lens assembly in the present example); a grid assembly 78 (for autofocusing); collimating/focusing lenses 80A and 80B, a beam splitter/combiner 82, and an imaging lens 84. Light from the light source 70 is directed by lenses and beam splitter to the pinhole mirror 23D which reflects this light towards the article. Light coming from the article is reflected by the pinhole mirror and then by the beam splitter 82 towards the detection unit 72. The use of a grid assembly for the autofocusing is described in U.S. Pat. No. 5,604,344 assigned to the assignee of the present application, and is incorporated herein by reference with respect to this specific example only. The operation of the imaging system does not form part of the present invention, and therefore need not be more specifically described.

Thus, the present invention provides for measuring/inspecting articles with a broad illuminating spectrum, i.e., from IR to DUV (or VUV), using essentially reflective optics. This is due to the novel configuration of the objective lens arrangement. This configuration also allows for implementing a telecentric optical system. The invention allows for measurement/inspection/imaging with polarized light, which is improved due to the novel configuration of a non-polarizing reflective objective lens arrangement and a polarization assembly using a polarizer and a compensator.

The present invention provides for spectrometry, spectrophotometry, reflectometry and ellipsometry measurement/inspection of articles, which is especially useful for patterned articles, for measuring the parameters of the pattern (e.g., thickness of layers). The invention also provides for scatterometric measurements of periodic patterned structures. It should be understood that the technique of the present invention may be in various applications, for example for measuring/inspecting semiconductor wafers, reticles, flat panel displays, etc. The system of the present invention has a compact configuration and can therefore be advantageously used as an integrated measurement system, for example being associated with a lithography tools arrangement, Chemical Mechanical Planarization (CMP) system, material deposition system (CVD, PVD), material removal system (etching tools arrangement), etc.

Those skilled in the art will readily appreciate that various modifications and changes can be applied to the embodiments of the invention as hereinbefore described without departing from its scope defined in and by the appended claims.

The invention claimed is:

1. An optical system for use in measurement/inspection of an article, the optical system comprising
an illuminator arrangement, and a light directing unit configured for focusing incident light beam from said illuminator arrangement onto an article under measurement/inspection at substantially normal incidence and for collecting light from the article,
said light directing unit comprising an objective arrangement comprising a first reflective element having a concave reflective surface and defining an optical axis of the incident light propagation towards the article, and a second substantially flat and at least partially reflective element spaced-apart from said first reflective element along said optical axis,
the second element being configured to allow light passage therethrough and being oriented with respect to the optical axis and the first element such that at a predetermined angle of incidence of the incident light beam from said illuminator arrangement onto the second element, so that said incident light beam is reflected onto the reflective surface of the first element and further reflected therefrom to pass through the second element and focus on the article.

2. The system of claim 1, wherein the concave reflective surface of said first reflective element is symmetric about the optical axis defined thereby.

3. The system of claim 2, wherein said first reflective element is a spherical mirror.

4. The system of claim 2, wherein said first reflective element is an aspheric mirror.

5. The system of claim 1, wherein said illuminator arrangement comprises at least one light source and light directing optics with an aperture stop, said aperture stop and the second element of the objective arrangement being located in conjugate planes.

6. The system of claim 1, wherein said illuminator arrangement comprises at least one light source and light directing optics, said light source being located in a plane conjugate with a plane of location of the article under measurement/inspection.

7. The system of claim 1, wherein said illuminator arrangement comprises at least one light source and light directing optics with a field stop, said field stop being located in a plane conjugate with a plane of location of the article under measurement/inspection.

8. The system of claim 7, wherein the light source and the field stop are located in conjugate planes.

9. The system of claim 1, wherein the second element is an apertured mirror oriented such that the optical axis passes through the aperture in said mirror, and at the predetermined angle of incidence of the input light beam onto the reflective surface of the second element, the input light beam is reflected onto the reflective surface of the first element and reflected therefrom towards the aperture in the second element.

10. The system of claim 9, wherein an outer surface of the second element and its inner surface defined by the aperture are substantially light absorbing.

11. The system of claim 1, wherein the second element is accommodated in a back focal plane of the first element.

12. The system of claim 1, comprising an optical polarizer unit for affecting state of polarization of said incident light beam and light collected from the article.

13. The system of claim 12, wherein the polarizer unit is mounted for rotation to vary an orientation of its preferred plane of polarization.

14. The system of claim 13, wherein the polarizer unit comprises a polarizer element and a compensator element, the compensator element being configured for shifting a propagation axis of a light beam impinging thereon towards an axis of rotation of the polarizer unit to thereby compensate for a shift of the beam propagation axis from the axis of rotation caused by the rotation of the polarizer unit.

15. The system of claim 14, wherein the compensator is configured substantially as a plane parallel plate and is tilted in relation to the optical axis to shift the beam propagation axis.

16. The system of claim 1, wherein the illuminator arrangement comprises first and second light sources and a light directing arrangement, the light directing arrangement being configured to combine first and second light portions produced by the first and second light sources, respectively, and direct combined light towards the article under measurements.

17. The system of claim 16, wherein the first and second light sources are configured to produce the first and second light portions of different overlapping wavelength ranges, respectively.

18. The system of claim 17, wherein the illuminator arrangement comprises all-reflective relay optics.

19. The system of claim 5, wherein the aperture of the illuminator has a double-aperture configuration with a central blocking region.

20. An on-axis optical system for use in measurement/inspection of an substantially planar article such as a semiconductor wafer, reticle or flat panel display, the on-axis optical system comprising
an illuminator arrangement with a light source assembly and an aperture assembly, a light directing unit configured for focusing incident light beam from said illuminator arrangement onto said article under measurement/inspection at substantially normal incidence and for collecting light from the article,
said light directing unit comprising an objective arrangement comprising a first element having a concave reflective surface and defining an optical axis of incident light propagation, and a second substantially flat and at least partially reflective element spaced-apart from the first element along the optical axis,
the second element being configured to allow light passage therethrough and being oriented with respect to the optical axis and the first element such that at a predetermined angle of incidence of the incident light beam from said illuminator arrangement onto the second element, so that said light beam is reflected onto the reflective surface of the first element and further reflected therefrom to pass through the second element and focus on the article,
said aperture of the illuminator arrangement and said second element being located in conjugate planes.

* * * * *